US008268890B2

(12) United States Patent
Wink et al.

(10) Patent No.: US 8,268,890 B2
(45) Date of Patent: Sep. 18, 2012

(54) METHOD OF TREATING ISCHEMIA/REPERFUSION INJURY WITH NITROXYL DONORS

(75) Inventors: David A. Wink, Hagerstown, MD (US); Martin Feelisch, Shreveport, LA (US); Pasquale Pagliaro, Turin (IT); David A. Kass, Columbia, MD (US); Nazareno Paolocci, Baltimore, MD (US); Katrina M. Miranda, Tucson, AZ (US); Jon M. Fukuto, Agoura, CA (US)

(73) Assignees: Johns Hopkins University, Baltimore, MD (US); The United States of America as represented by the Secretary of Health and Human Services, Washington, WA (US); The Regents of the University of California, Los Angeles, CA (US)

( * ) Notice: Subject to any disclaimer, the term of this patent is extended or adjusted under 35 U.S.C. 154(b) by 90 days.

(21) Appl. No.: 12/346,694

(22) Filed: Dec. 30, 2008

(65) Prior Publication Data

US 2009/0246296 A1 Oct. 1, 2009

Related U.S. Application Data

(63) Continuation of application No. 10/463,084, filed on Jun. 16, 2003, now abandoned.

(60) Provisional application No. 60/388,819, filed on Jun. 14, 2002, provisional application No. 60/389,757, filed on Jun. 17, 2002.

(51) Int. Cl.
*A61K 31/13* (2006.01)
(52) U.S. Cl. .................................. 514/579; 514/645
(58) Field of Classification Search ........................ None
See application file for complete search history.

(56) References Cited

U.S. PATENT DOCUMENTS

| | | | |
|---|---|---|---|
| 4,539,321 | A | 9/1985 | Campbell |
| 4,954,526 | A | 9/1990 | Keefer |
| 5,039,705 | A | 8/1991 | Keefer et al. |
| 5,212,204 | A | 5/1993 | Keefer et al. |
| 5,789,447 | A | 8/1998 | Wink, Jr. et al. |
| 5,814,656 | A | 9/1998 | Saavedra et al. |
| 6,083,515 | A | 7/2000 | Garvey et al. |
| 6,143,734 | A | 11/2000 | Garvey et al. |
| RE37,116 | E | 3/2001 | Garvey et al. |
| 6,297,260 | B1 | 10/2001 | Bandarage et al. |
| 6,323,234 | B1 | 11/2001 | Garvey et al. |
| 6,936,639 | B2 | 8/2005 | Wink et al. |
| 2002/0010146 | A1 | 1/2002 | Garvey et al. |
| 2002/0016322 | A1 | 2/2002 | Bandarage et al. |
| 2002/0119977 | A1 | 8/2002 | Khanapure et al. |
| 2004/0038947 | A1 | 2/2004 | Wink et al. |
| 2005/0192254 | A1 | 9/2005 | Wink et al. |

FOREIGN PATENT DOCUMENTS

| | | |
|---|---|---|
| WO | WO-96/32946 A1 | 10/1996 |
| WO | WO-98/43621 A1 | 10/1998 |
| WO | WO-99/33823 A1 | 7/1999 |
| WO | WO-00/28988 A1 | 5/2000 |
| WO | WO-00/67754 A1 | 11/2000 |
| WO | WO-01/45703 A1 | 6/2001 |
| WO | WO-02/060378 A2 | 8/2002 |
| WO | WO-02/060378 A3 | 8/2002 |
| WO | WO-2005/074598 A2 | 8/2005 |
| WO | WO-2005/074598 A3 | 8/2005 |

OTHER PUBLICATIONS

Adams et al., "Heart Failure Society of America (HFSA) Practice Guidelines. HFSA Guidelines for Management of Patients With Heart Failure Caused by Left Ventricular Systolic Dysfunctions—Pharmacological Approaches," Heart Failure Society of America, pp. 1-36 (1999).
Advisory Action, U.S. Appl. No. 10/463,084 (published as US 2004-0038947 A1) (May 25, 2007).
Amendment submitted in response to Final Office Action, U.S. Appl. No. 10/463,084 (published as US 2004-0038947 A1) (May 8, 2007).
Amendment submitted with Request for Continued Examination, U.S. Appl. No. 10/463,084 (published as US 2004-0038947 A1) (Apr. 10, 2008).
Anonymous, Sections 1-15 of *Pocket Guide HFSA 2006 Comprehensive Heart Failure Practice Guideline*, Heart Failure Society of America, pp. 1-95 (2006).
Anonymous, "The 2001 Canadian Cardiovascular Society Consensus Guideline Update for the Management and Prevention of Heart Failure," The Canadian Cardiovascular Society, 28 pages (2001).
Bassani et al., "Na-Ca Exchange is Required for Rest-decay but not for Rest-potentiation of Twitches in Rabbit and Rat Ventricular Myocytes," *J. Mol. Cell. Cardiol.*, 26(10):1335-1347 (Oct. 1994).
Bazylinski et al., "Evidence from the Reaction Between Trioxodinitrate(II) and $^{15}$NO That Trioxodinitrate (II) Decomposes into Nitrosyl Hydride and Nitrite in Neutral Aqueous Solution," *Inorg. Chem.*, 24(25):4285-4288 (Dec. 1985).
Bazylinski et al., "Metmyoglobin and Methemoglobin as Efficient Traps for Nitrosyl Hydride (Nitroxyl) in Neutral Aqueous Solution," *J. Am. Chem. Soc.*, 107(26):7982-7986 (1985).
Bonner et al., "The Aqueous Solution Chemistry of Nitrogen in Low Postive Oxidation States," *Comments Inorg. Chem.*, 7(4):215-234 (1988).
Bristow, "β-Adrenergic Receptor Blockade in Chronic Heart Failure," *Circulation*, 101(5):558-569 (Feb. 8, 2000).
Chavey et al., "Guideline for the Management of Heart Failure Caused by Systolic Dysfunction: Part II. Treatment," *American Family Physician*, 64(6):1045-1054 (Sep. 15, 2001).
Cheng et al., "Amplitude Distribution of Calcium Sparks in Confocal Images: Theory and Studies with an Automatic Detection Method," *Biophys. J.*, 76(2):606-617 (Feb. 1999).

(Continued)

*Primary Examiner* — Renee Claytor
(74) *Attorney, Agent, or Firm* — Arnold & Porter LLP; Suet Chong

(57) ABSTRACT

Nitroxyl donating compounds are administered prior to the onset of ischemia for the prevention and/or reduction of ischemia/reperfusion injury in subjects at risk for ischemia. Nitroxyl donors also are administered to organs to be transplanted for the prevention and/or reduction of ischemia/reperfusion injury upon reperfusion in a recipient. Nitroxyl donors include any nitroxyl donating compound. In particular cases the nitroxyl donor is a nitroxyl-donating diazeniumdiolate, such as Angeli's salt or IPA/NO.

56 Claims, 5 Drawing Sheets

OTHER PUBLICATIONS

Cheong et al., "Nitroxyl triggers $Ca^{2+}$ release from skeletal and cardiac sarcoplasmic reticulum by oxidizing ryanodine receptors," *Cell Calcium*, 37(1):87-96 (Jan. 2005).

Colton, "Nitroxyl anion regulation of the NMDA receptor," *J. Neurochem.*, 78(5):1126-1134 (Sep. 2001).

Colucci et al., "Treatment of acute decompensated heart failure," located at http://www.utdol.com.ezproxy.welch.jhmi.edu/online/content/ topic.do?to..., 26 pages (last updated Jun. 14, 2009; last visited Aug. 10, 2009).

Cortassa et al., "A Mitochondrial Oscillator Dependent on Reactive Oxygen Species," *Biophys. J.*, 87(3):2060-2073 (Sep. 2004).

Díaz et al., "The control of sarcoplasmic reticulum Ca content in cardiac muscle," *Cell Calcium*, 38(3-4):391-396 (Sep./Oct. 2005).

DiDomenico et al., "Guidelines for Acute Decompensated Heart Failure Treatment," *The Annals of Pharmacotherapy*, 38(4):649-660 (Apr. 2004, e-published Feb. 24, 2004).

Dostal et al., "Detection of angiotensin I and II in cultured rat cardiac myocytes and fibroblasts," *Am. J. Physiol.*, 263(4-Pt. 1):C851-C863 (Oct. 1992).

Doyle et al., "Oxidation and Reduction of Hemoproteins by Trioxodinitrate(II). The Role of Nitrosyl Hydride and Nitrite," *J. Am. Chem. Soc.* 110 (2):593-599 (1988).

Feelisch, "Nitroxyl gets to the heart of the matter," *Proc. Natl. Acad. Sci. USA*, 100(9):4978-4980 (Apr. 29, 2003; e-pub. Apr. 18, 2003).

Feld et al., "Future strategies for the treatment of diastolic heart failure," *Acute Cardiac Care*, 8(1):13-20 (2006).

Felker et al., "Heart Failure Etiology and Response to Milrinone in Decompensated Heart Failure," *J. Am. Coll. Card.*, 41(6):997-1003 (Mar. 19, 2003).

Felker et al., "Risk Stratification After Hospitalization for Decompensated Heart Failure," *J. Card Fail.*, 10(6):460-466 (Dec. 2004).

Final Office Action, U.S. Appl. No. 10/463,084 (published as US 2004-0038947 A1) (Mar. 8, 2007).

Franklin et al., "Prognosis in Diastolic Heart Failure," *Prog. Cardiovasc. Dis.*, 47(5):333-339 (Mar./Apr. 2005).

Froehlich et al., "Studies of Sarcoplasmic Reticulum Function and Contraction Duration in Young Adult and Aged Rat Myocardium," *J. Mol. Cell. Cardiol.*, 10(5):427-438 (1978).

Fukuto et al., "The Physiological Chemistry and Biological Activity of Nitroxyl (HNO): The Neglected, Misunderstood, and Enigmatic Nitrogen Oxide," *Chem. Res. Toxicol.*, 18(5):790-801 (May 2005).

Gheorghiade et al., "Acute Heart Failure Syndromes," *J. Am. Coll. Card*, 53(7):557-573 (Feb. 17, 2009).

Hain et al., "Phosphorylation Modulates the Function of the Calcium Release Channel of Sarcoplasmic Reticulum from Cardiac Muscle," *J. Biol. Chem.*, 270(5):2074-2081 (Feb. 3, 1995).

Hunt et al., "ACC/AHA Guidelines for the Evaluation and Management of Chronic Heart Failure in the Adult," *the American College of Cardiology and the American Heart Association, Inc.*, pp. 1-56 (2001).

International Search Report, International Application No. PCT/US2006/024545 (published as WO 2007/002444) (mailed Nov. 17, 2006).

Jiang et al., "Abnormal $Ca^{2+}$ Release, but Normal Ryanodine Receptors, in Canine and Human Heart Failure," *Circ. Res.*, 91(11):1015-1022 (Nov. 29, 2002; e-pub. Oct. 24, 2002).

Kass et al., "What Mechanisms Underlie Diastolic Dysfunction in Heart Failure?" *Cir. Res.*, 94(12):1533-1542 (Jun. 25, 2004).

Kass, "Assessment of Diastolic Dysfunction: Invasive Modalities," *Cardiol. Clin.*, 18(3):571-586 (Aug. 2000).

Kass, "Rescuing a Failing Heart," *Nature Medicine*, 15(11):24-25 (Jan. 2009).

Katori et al., "The Novel Organic Nitroxyl Donor, Isopropylamine/Nitric Oxide Exerts Beta-Independent Positive Inotropy/Lusitropy in Failing Hearts," Poster, *presented at American College of Cardiology on* Mar. 9, 2004, New Orleans, Louisiana, *J Am. Coll. Cardiol.*, 43(5):218A, Abstract 1144-104 (Mar. 3, 2004).

Khan et al., "Managed Care Interventions for Improving Outcomes in Acute Heart Failure Syndromes," *The American Journal of Managed Care*, 14(9):S273-S286 (Dec. 2008).

Kim et al., "Attenuation of NMDA Receptor Activity and Neurotoxicity by Nitroxyl Anion, NO'," *Neuron*, 24(2):461-469 (Oct. 1999).

King et al., "[22] Chemical Approaches Toward Generation of Nitroxyl," *Methods in Enzymology*, 301:211-220 (1999).

Kohout et al., "On the Role of the Nitroxyl Molecule in the Reaction of Hydrogen Atoms with Nitric Oxide," *J Am. Chem. Soc.*, 87(24):5795-5796 (Dec. 20, 1965).

Kubalova et al., "Abnormal intrastore calcium signaling in chronic heart failure," *Proc. Natl. Acad. Sci. USA*, 102(39):14104-14109 (Sep. 27, 2005; e-pub. Sep. 19, 2005).

Little, "The Left Ventricular $dP/dt_{max}$-End-Diastolic Volume Relation in Closed-Chest Dogs," *Circ. Res.*, 56(6):808-815 (Jun. 1985).

MacLennan et al., "Phospholamban: A Crucial Regulator of Cardiac Contractility," *Nat. Rev. Mol. Cell Biol.*, 4(7):566-577 (Jul. 2003).

Mahaney et al., "Intermolecular Conformational Coupling and Free Energy Exchange Enhance the Catalytic Efficency of Cardiac Muscle SERCA2a following the Relief of Phospholamban Inhibition," *Biochemistry*, 44(21):7713-7724 (May 31, 2005; e-pub. May 5, 2005).

Matter et al., "Effect of NO Donors on LV Diastolic Function in Patients With Severe Pressure-Overload Hypertrophy," *Circulation*, 99(18):2396-2401 (May 11, 1999).

Mongillo et al., "Compartmentalized Phosphodiesterase-2 Activity Blunts β-Adrenergic Cardiac Inotropy via an NO/cGMP-Dependent Pathway," *Circ. Res.*, 98(2):226-234 (Feb. 3, 2006; e-pub. Dec. 15, 2005).

Nieminen et al., "Executive summary of the guidelines on the diagnosis and treatment of acute heart failure—The Task Force on Acute Heart Failure of the European Society of Cardiology," *Eur. Heart J.*, 26(4):384-416 (Feb. 2005, e-published Jan. 28, 2005).

Non-final Office Action, U.S. Appl. No. 10/463,084 (published as US 2004-0038947 A1) (Jul. 2, 2008).

Owan et al., "Epidemiology of Diastolic Heart Failure," *Prog. Cardiovasc. Dis.*, 47(5):320-332 (Mar./Apr. 2005).

Paolocci et al., "The cardiovascular effects of HNO/nitroxyl," *Nitric Oxide*, 6(4):445, Abstract (Jun. 2002).

Paulus et al., "Myocardial Contractile Effects of Nitric Oxide," *Heart Fail. Rev.*, 7(4):371-383 (Oct. 2002).

Petersen et al., "Inotropes in the management of acute heart failure," *Crit. Care Med.*, 36(1)(Suppl.):S106-S111 (Jan. 2008).

Prestle et al., "$Ca^{2+}$-Handling Proteins and Heart Failure: Novel Molecular Targets?" *Curr. Med. Chem.*, 10(11):967-981 (Jun. 2003).

Quiñones, "Assessment of Diastolic Function," *Prog. Cardiovasc. Dis.*, 47(5):340-355 (Mar./Apr. 2005).

Remme et al., "Guidelines for the diagnosis and treatment of chronic heart failure," *Eur. Heart J.*, 22:1527-1560 (2001).

Schmidt et al., "No •NO from NO Synthase," *Proc. Natl. Acad. Sci. USA*, 93(25):14492-14497 (Dec. 10, 1996).

Senzaki et al., "Improved Mechanoenergetics and Cardiac Rest and Reserve Function of in Vivo Failing Heart by Calcium Sensitizer EMD-57033," *Circulation*, 101(9):1040-1048 (Mar. 7, 2000).

Shafirovich et al., "Nitroxyl and its anion in aqueous solutions; Spin states, protic equilibria, and reactivities toward oxygen and nitric oxide," *Proc. Natl. Acad. Sci. USA*, 99(11):7340-7345 (May 2002).

Sham et al., "Termination of $Ca^{2+}$ release by a local inactivation of ryanodine receptors in cardiac myocytes," *Proc. Natl. Acad. Sci. USA*, 95(25):15096-15101 (Dec. 8, 1998).

Sharpe et al., "Reactions of nitric oxide with mitochondrial cytochrome *c*: a novel mechanism for the formation of nitroxyl anioon and peroxynitrite," *Biochem. J.*, 332(1):9-19 (May 15, 1998).

Shin et al., "Review of Current and Investigational Pharmacologic Agents for Acute Heart Failure Syndromes," *Am. J. Cardiol.*, 99(2A):4A-23A (Jan. 22, 2007, e-published Nov. 27, 2006).

Smith et al., "The Alleged Role of Nitroxyl in Certain Reactions of Aldehydes and Alkyl Halides," *J. Am. Chem. Soc.*, 82:5731-5740 (1960).

Stoyanovsky et al., "Nitric oxide activates skeletal and cardiac ryanodine receptors," *Cell Calcium*, 21(1):19-29, (Abstract only) (Jan. 1997).

Tocchetti et al., "Nitroxyl Improves Cellular Heart Function by Directly Enhancing Cardiac Sarcoplasmic Reticulum $Ca^{2+}$ Cycling," *Circulation Research*, 100(1):96-104 (Jan. 5, 2007, e-pub. Nov. 30, 2006).

Written Opinion, International Application No. PCT/US2006/024545 (now International Publication No. WO 2009/002444) (mailed Nov. 17, 2006).
Xu et al., "Activation of the Cardiac Calcium Release Channel (Ryanodine Receptor) by Poly-S-Nitrosylation," *Science*, 279(5348):234-237 (Jan. 9, 1998).
Yturralde et al., "Diagnostic Crieria for Diastolic Heart Failure," *Prog. Cardiovasc. Dis.*, 47(5):314-319 (Mar./Apr. 2005).
Zaccolo et al., "Discrete Microdomains with High Concentration of cAMP in Stimulated Rat Neonatal Cardiac Myocytes," *Science*, 295(5560):1711-1715 (Mar. 1, 2002).
Zahradníková et al., "Inactivation of the Cardiac Ryanodine Receptor Calcium Release Channel by Nitric Oxide," *Cell Calcium*, 22(6):447-453 (Dec. 22, 1997).
Zhou et al., "Constitutive $\beta_2$-Adrenergic Signalling Enhances Sarcoplasmic Reticulum $Ca^{2+}$ Cycling to Augment Contraction in Mouse Heart," *J. Physiol.*, 52(Pt. 2):351-361 (Dec. 1, 1999).
Zile et al., "Diastolic heart failure: definitions and terminology," *Prog. Cardiovasc. Dis.*, 47(5):307-313 (Mar./Apr. 2005).
Ziolo et al., "Positive and negative effects of nitric oxide on $Ca^{2+}$ sparks: influence of $\beta$-adrenergic stimulation," *Am. J. Physiol. Heart Circ. Physiol.*, 281(6):H2295-H2303 (Dec. 2001).
De Witt, B.J. et al. (Nov. 2, 2001). "Comparison of Responses to Novel Nitric Oxide Donors in the Feline Pulmonary Vascular Bed," *Eur. J. Pharmacol.* 430(2-3):311-315.
Fitzhugh, A.L. et al. (May 15, 2000). "Diazeniumdiolates: Pro- and Antioxidant Applications of the 'NONOates'," *Free Radic. Biol. Med.* 28(10):1463-1469.
Fukuto, J.M. et al. (Nov. 1992). "The Pharmacological Activity of Nitroxyl: A Potent Vasodilator with Activity Similar to Nitric Oxide and/or Endothelium-Derived Relaxing Factor," *J. Pharmacol. Exp. Ther.* 263(2):546-551.
Fukuto, J.M. et al. (2005). "Nitroxyl (HNO): Chemistry, Biochemistry, and Pharmacology," *Annu. Rev. Pharmacol. Toxicol.* 45:335-355.
Fukuto, J.M. et al. (Apr. 2005). "The Chemistry and Biology of Nitroxyl (HNO): A Chemically Unique Species with Novel and Important Biological Activity," *Chembiochem.* 6(4):612-619.
Gelvan, D. et al. (Jun. 1, 1991). "Cardiac Reperfusion Damage Prevented by a Nitroxide Free Radical," *Proc. Natl. Acad. Sci. USA* 88(11):4680-4684.
Hart, C.Y. et al. (Jul. 2001). "Differential Effects of Natriuretic Peptides and NO on LV Function in Heart Failure and Normal Dogs," *Am. J. Physiol. Heart Circ. Physiol.*, 281(1):H146-H154 (Abstract Only).
Isselbacher, K.J. et al., eds. (1994). "Treatment of Heart Failure," in *Harrison's Principles of Internal Medicine*, 13$^{th}$ Edition, McGraw-Hill, Inc.: New York, NY, pp. 1002-1008.
Li, H. et al. (Apr. 15, 2002). "Polynitroxyl-Albumin (PNA) Enhances Myocardial Infarction Therapeutic Effect of Tempol in Rat Hearts Subjected to Regional Ischemia-Reperfusion," *Free Radic. Biol. Med.* 32(8):712-719.
Ma, X.L. et al. ((Dec. 7, 1999). "Opposite Effects of Nitric Oxide and Nitroxyl on Postischemic Myocardial Injury," *Proc. Natl. Acad. Sci. USA* 96(25):14617-14622.
Maragos, C.M. et al. (Nov. 1991). "Complexes of 'NO with Nucleophiles as Agents for the Controlled Biological Release of Nitric Oxide. Vasorelaxant Effects," *J. Med. Chem.* 34(11):3242-3247.

Miranda, K.M. et al. (2005). "Donors of HNO," *Curr. Top. Med. Chem.* 5(7):649-664.
Naughton, P. et al. (2001). "Induction of Haem Oxygenase-1 by Nitroxyl Anion ($NO^-$) in Cardiomyocytes," *J. Physiol* 531:194P.
Pagliaro, P. (Sep. 12, 2003). "Differential Biological Effects of Products of Nitric Oxide (NO) Synthase: It is Not Enough to Say NO," *Life Sci.* 73(17):2137-2149.
Pagliaro, P. et al. (2001). "Is Nitroxyl Anion Involved in Myocardial Protection Against Ischaemia/Reperfusion Injury in Isolated Rat Hearts?" *J. Physiol.* 536:143P.
Pagliaro, P. et al. (2001). "Nitroxyl Anion is a Preconditioning Agent in Isolated Rat Heart," *Circulation* 104(17 Suppl.):II-263-II-264, Abstract 1265.
Pagliaro, P. et al. (2003). "Nitroxyl Affords Thiol-Sensitive Myocardial Protective Effects Akin to Early Preconditioning," *Free Radic. Biol. Med.* 34(1):33-43.
Paolocci, N. et al. (Aug. 28, 2001; e-pub. Aug. 21, 2001). "Nitroxyl Anion Exerts Redox-Sensitive Positive Cardiac ;Inotropy in Vivo by Calcitonin Gene-Related Peptide Signaling," *Proc. Natl. Acad. Sci. USA* 98(18):10463-10468.
Paolocci, N. et al. (Sep. 2001). "Nitroxyl Anion Improves in Vivo Contractile Function and Promotes Active Relaxation in Experimental Heart Failure," *Italian Heart Journal* 2(Suppl. 3):62S, Abstract No. 38.
Paolocci, N. et al. (Apr. 29, 2003). "Positive Inotropic and Lusitropic Effects of $HNO/NO^-$ in Failing Hearts: Independence from $\beta$-Adrenergic Signaling," *Proc. Natl. Acad. Sci. USA* 100(9):5537-5542.
Paolocci, N. et al. (Feb. 2007; e-pub. Nov. 29, 2006). "The Pharmacology of Nitroxyl (HNO) and its Therapeutic Potential: Not Just the Janus Face of NO," *Pharmacology and Therapeutics* 113(2): 442-458.
Takahira, R. et al. (Sep. 15, 2001). "Dexamethasone Attenuates Neutrophil Infiltration in the Rat Kidney in Ischemia/Reperfusion Injury: The Possible Role of Nitroxyl," *Free Radic. Biol. Med.* 31(6):809-815.
Thomas, D.D. et al. (2002). "Guide for the Use of Nitric Oxide (NO) Donors as Probes of the Chemistry of NO and Related Redox Species in Biological Systems," Chapter 8, in *Methods in Enzymology*, Academic Press: Amsterdam, 359:84-105.
Tosaki, A. et al. (Nov.-Dec. 1992). "Does the Antiarrhythmic Effect of DMPO Originate from its Oxygen Radical Trapping Property or the Structure of the Molecule Itself?" *Basic Res. Cardiol.* 87(6):536-547.
Vanuffelen, B.E. et al. (Mar. 1, 1998). "Intracellular but not Extracellular Conversion of Nitroxyl Anion into Nitric Oxide Leads to Stimulation of Human Neutrophil Migration," *Biochem. J.* 330(Pt. 2):719-722.
Wink, D.A. et al. (Dec., 2003; first published Jul. 10, 2003). "Orthogonal Properties of the Redox Siblings Nitroxyl and Nitric Oxide in the Cardiovascular System: a Novel Redox Paradigm," *Am. J. Physiol. Heart Circ. Physiol.* 285:H2264-H2276.
Yu, L. et al. (Mar. 1, 1994). "Nitric Oxide: A Mediator in Rat Tubular Hypoxia/Reoxygenation Injury," *Proc. Natl. Acad. Sci. USA* 91(5):1691-1695.
U.S. Appl. No. 10/587,644, filed Jul. 27, 2006, by Toscano et al.
U.S. Appl. No. 11/922,793, filed Dec. 21, 2007, by Paolocci et al.
Csonka et al., "Classic Preconditioning Decreases the Harmful Accumulation of Nitric Oxide During Ischemia and Reperfusion in Rat Hearts", *Circulation*, 100:2260-2266 (1999).
Zweier et al., "Non-enzymatic nitric oxide synthesis in biological systems", *Biochimica et Biophysica Acta*, 1411:250-262 (1999).

Developed LVP dP/dt$_{max}$

METHOD OF TREATING ISCHEMIA/REPERFUSION INJURY WITH NITROXYL DONORS

CROSS REFERENCE TO RELATED APPLICATIONS

This application is a continuation application, under 35 U.S.C. §120, of U.S. patent application Ser. No. 10/463,084, filed Jun. 16, 2003, which claims the benefit of the earlier filing dates of prior U.S. Provisional Patent Application No. 60/388,819, filed Jun. 14, 2002, and U.S. Provisional Patent Application No. 60/389,757, filed Jun. 17, 2002, the disclosures of which are incorporated herein by reference in their entirety.

FIELD

Compounds and compositions are disclosed that are useful to prevent or protect against injury caused by ischemia and reperfusion.

BACKGROUND

Ischemia is a condition characterized by an interruption or inadequate supply of blood to tissue, which causes oxygen deprivation in the affected tissue. Myocardial ischemia is a condition caused by a blockage or constriction of one or more of the coronary arteries, such as can occur with atherosclerotic plaque occlusion or rupture. The blockade or constriction causes oxygen deprivation of the non-perfused tissue, which can cause tissue damage. Further, upon reperfusion with subsequent reoxygenation of the tissue, when the blood is able to flow again or the oxygen demand of the tissue subsides, additional injury can be caused by oxidative stress.

Ischemia/reperfusion injury refers to tissue damage caused by oxygen deprivation followed by reoxygenation. The effects of ischemia/reperfusion injury in a subject experiencing the condition can be fatal, particularly when the injury occurs in a critical organ such as the heart or brain.

Accordingly, compounds and compositions effective in preventing or protecting against ischemia/reperfusion would be useful pharmaceuticals. Compounds such as nitroglycerin have been used for a long period of time to help control vascular tone and protect against myocardial ischemia/reperfusion injury. However, the cause of nitroglycerin's therapeutic effect was not known until late in the last century when it was discovered that the nitric oxide molecule ($NO^-$) was responsible for nitroglycerin's beneficial effects. In fact, the Nobel Prize was awarded in 1998 to three researchers who discovered $NO^-$'s beneficial effects.

This discovery prompted interest in medical uses for $NO^-$ and investigations into related species such as nitroxyl ($HNO/NO^-$), the one-electron reduction product of $NO^-$. Angeli's salt (sodium trioxodinitrate or $Na_2N_2O_3$) is a compound that decomposes to donate nitroxyl. Fitzhugh & Keefer, "Forum: Therapeutic Applications of Reactive Oxygen and Nitrogen Species in Human Disease," *Free Radical Biology & Medicine*, 28(10): 1463-1469 (2000). U.S. Pat. No. 5,212,204 describes the vasodilating properties of $NO^-$ and discloses a pharmaceutical composition consisting essentially of Angeli's salt and a pharmaceutically acceptable sterile carrier, which the patent states can be useful to treat cardiac diseases that would respond favorably to a decrease in blood pressure, such as hypertension.

However, experiments testing the ability of Angeli's salt to prevent or protect against ischemia/reperfusion injury demonstrated that $NO^-$ increases ischemia/reperfusion injury. For example, Ma et al., "Opposite Effects of Nitric Oxide and Nitroxyl on Postischemic Myocardial Injury," *Proc. Nat'l Acad. Sci.*, 96(25):14617-14622 (1999) reported that administration of Angeli's salt to anesthetized rabbits during ischemia and 5 minutes prior to reperfusion increased myocardial ischemia/reperfusion injury. Also, Takahira et al., "Dexamethasone Attenuates Neutrophil Infiltration in the Rat Kidney in Ischemia/Reperfusion Injury: The Possible Role of Nitroxyl," *Free Radical Biology & Medicine*, 31(6):809-815 (2001) reported that administration of Angeli's Salt during ischemia and 5 minutes before reperfusion of rat renal tissue contributed to neutrophil infiltration into the tissue, which is believed to mediate ischemia/reperfusion injury.

Thus, no effective therapy using nitroxyl to prevent or protect against ischemia/reperfusion injury has been developed.

SUMMARY

The inventors have discovered that administration of a nitroxyl donating compound, prior to ischemia, can attenuate ischemia/reperfusion injury to tissues, for example, myocardial tissues. This beneficial effect is a surprising result given that nitroxyl was previously reported to increase ischemia/reperfusion injury. In particular, it has been demonstrated that pre-ischemic administration of Angeli's salt and isopropylamine/NO can prevent or reduce ischemia/reperfusion injury.

The beneficial effect appears to be dependent on the timing of administration. In previous studies, discussed above, a nitroxyl donor was administered after the onset of ischemia. The results demonstrated that nitroxyl increased the injury resulting from ischemia and reperfusion. However, when administered prior to an ischemic event, nitroxyl unexpectedly protects tissue from damage associated with ischemia and reperfusion.

Accordingly, nitroxyl donating compounds such as Angeli's salt (which decomposes to $HNO/NO^-$) are useful treatment agents to prevent or protect against ischemia/reperfusion injury. In particular, these agents are beneficial for subjects at risk for an ischemic event. Thus, provided herein is a method of preventing or reducing the injury associated with ischemia/reperfusion by administering a therapeutically effective dose of at least one nitroxyl donating compound to a subject prior to the onset of ischemia. Also provided is a similar method in which the subject is demonstrated to be at risk for an ischemic event. Also disclosed is a method of administering nitroxyl to an organ that is to be transplanted in a dose effective to reduce ischemia/reperfusion injury to the tissues of the organ upon reperfusion in the recipient of the transplanted organ.

These and other features, aspects, and advantages of the disclosed method will become more apparent and better understood with regard to the following figures and description.

BRIEF DESCRIPTION OF THE FIGURES

FIG. 2A is a graph showing the change in left ventricular end-diastolic pressure (LVEDP) between pre-ischemic values and the end of the 30 minute ischemia for interventions in isolated rats hearts with control; AS; DEA/NO; IPC; vehicle; NAC; and NAC+AS.

DETAILED DESCRIPTION

Figure 1:
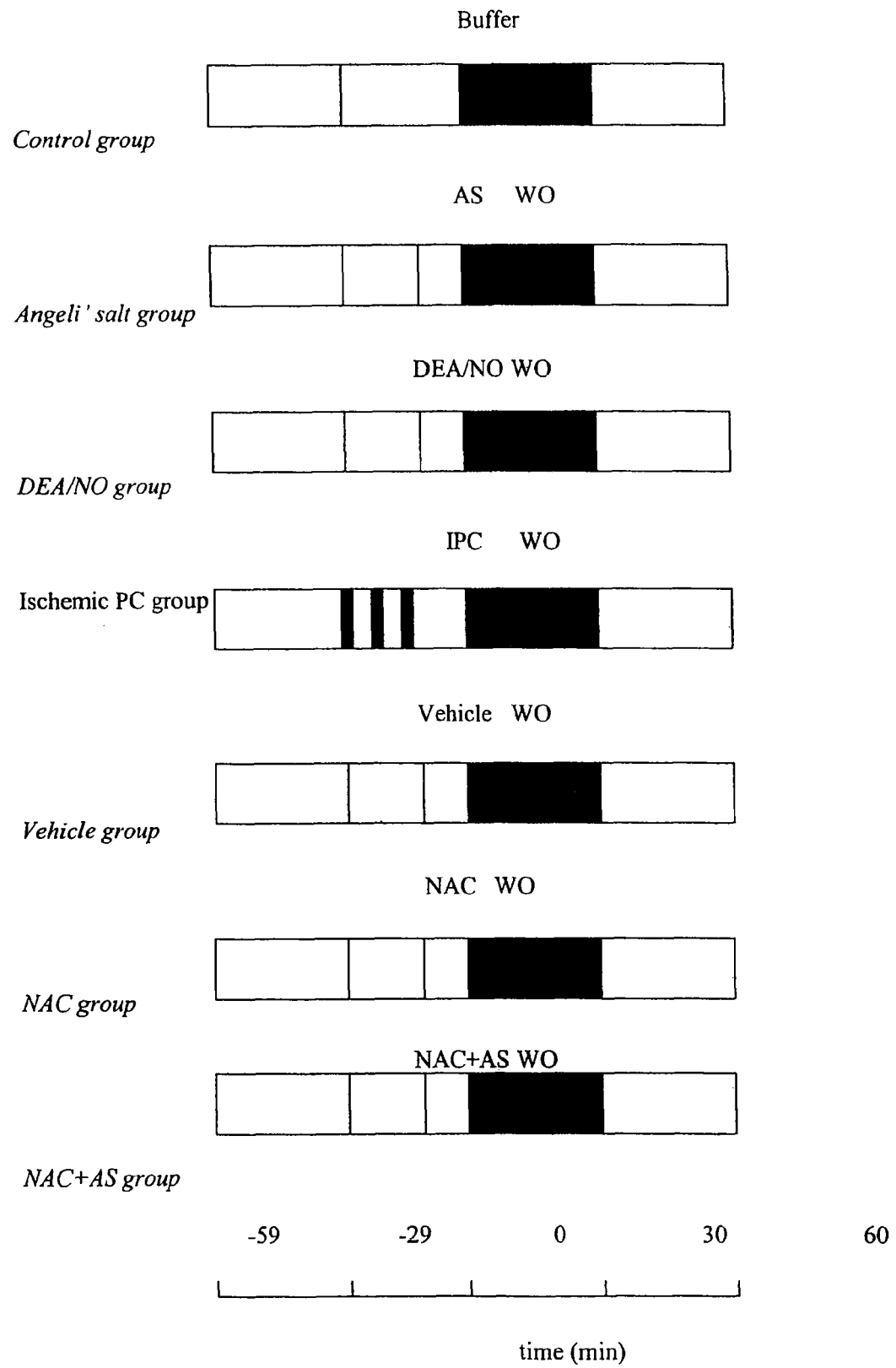
FIG. 1 shows the timing of interventions with control; Angeli's salt (AS); diethylamine/NO (DEA/NO); ischemic preconditioning (IPC); vehicle; N-acetyl-L-cysteine (NAC); and NAC+AS, in relation to stabilization, washout (WO), the onset of ischemia (black shaded sections), and reperfusion in the protocols for which results are shown in the following figures.

A "subject" is an animal, such as a mammal, for example, a human.

"Nitroxyl" is HNO/NO⁻.

"NO⁻" is the free radical nitric oxide.

A "nitroxyl donor" is an agent or compound (or combination of agents or compounds) that donates nitroxyl.

"Nitroxyl donation pH" is the pH at which and above which a nitroxyl-donating compound donates nitroxyl.

"Aliphatic" refers to substituted or unsubstituted alkanes, alkenes, alkynes, their cycloalkyl analogs, and combinations thereof.

"Aryl" refers to substituted or unsubstituted hydrocarbon groups forming aromatic rings, such as phenyl, naphthyl, pyrrolyl, pyridinyl, quinolinyl, and isoquinolinyl.

"Aryl-aliphatic" refers to any aryl group substituted by an aliphatic group, such as alkyl, for example a lower alkyl (also referred to as arylalkyl).

"Alkyl" refers to branched and straight chain hydrocarbons.

"Lower alkyl" refers to branched and straight chain hydrocarbons of from one to ten carbons inclusive, and is exemplified by such groups as propyl, isopropyl, butyl, 2-butyl, t-butyl, amyl, isoamyl, hexyl, heptyl, and octyl.

"Cycloalkyl" refers to cyclic alkanes, for example those having from one to ten carbons, such as cyclopropyl, cyclopentyl, cyclohexyl, cycloheptyl, and cyclooctyl.

An NSAID is a non-steroidal anti-inflammatory drug, such as, for example salicylic acid derivatives (for example, acetylsalicylic acid, diflunisal, salicylsalicylic acid), pyrazolon derivatives (for example, phenylbutazone, oxyphenbutazone, antipyrine and aminopyrine), para-aminophenol derivatives (for example, phenacetin and its active metabolite acetominaphin), propionic acid derivatives (for example, ibuprofen, naproxen, and flurbiprofen), celocoxib and rofecoxib.

A "biomolecule" is an organic molecule, whether naturally occurring, recombinantly produced, or chemically synthesized in whole or in part, that is, was or can be a part of a living organism. The term encompasses, for example, nucleotides, nucleosides, amino acids and monosaccharides, as well as oligomeric and polymeric species such as oligonucleotides and polynucleotides, peptidic molecules such as oligopeptides, polypeptides and proteins, saccharides such as disaccharides, oligosaccharides, polysaccharides, mucopolysaccharides and peptidoglycans (peptido-polysaccharides). In particular cases, the biomolecule has an affinity for the cells of particular tissues, such as a neuropeptide, for example calcitonin gene related peptide (CGRP).

"Amine" or "amine group" refers to primary (NHR) or secondary (NR$_2$) groups wherein $R_1$ and $R_2$ are organic groups such as aliphatic, aryl, or aryl-aliphatic substituted or unsubstituted hydrocarbons, NSAIDS, and biomolecules.

"Substituted" refers to the attachment of one or more organic substituents to a particular group, such as attachment of an aliphatic, aryl, or aryl-aliphatic substituted or unsubstituted hydrocarbon, or an inorganic group such as a halogen group, for example I, Br, Cl, or F, or a nitro ($NO_2$) group.

"Unsubstituted" refers to a group that does not have additional substituents.

A "pharmaceutically acceptable cation" refers to any cation that does not render the compound unstable or toxic at contemplated dosages. Typically the cation is a group 1 or group 2 ion, such as sodium, potassium, calcium, and magnesium, for example, $Na^+$, $K^+$, $Ca^{2+}$, and $Mg^{2+}$.

A "therapeutically effective dose" is a dose that prevents or reduces tissue injury following ischemia and reperfusion.

"Organ" means a part of an animal, such as a mammal, for example a human, which is composed of several tissues and adapted to perform a specific function or functions. Examples of organs include the heart, lung, kidney, and liver.

"Transplanting an organ" means removing an organ from one individual (known as the donor) and inserting the organ into a different individual (known as the recipient).

Nitroxyl can be provided directly as HNO/NO⁻, but typically is provided with the use of a nitroxyl donor.

In some examples the nitroxyl donor is a nitroxyl-donating diazeniumdiolate. A diazeniumdiolate is a compound having the formula J-N(O)NO wherein J is any moiety. These compounds are generally known as diazeniumdiolates because they contain the N-oxy-N-nitroso (NONO) complex. Some diazeniumdiolates donate nitroxyl. These are referred to as nitroxyl-donating diazeniumdiolates. Such compounds include any compound where J is any moiety such that the compound donates nitroxyl. Examples of such compounds used in the disclosed methods have the formula:

$$\left( J\diagdown\underset{\underset{N\diagdown\diagdown O}{\overset{|}{N}}}{N}\diagup O^-\right) M_c^{+x}$$

wherein J is oxide (O⁻), sulfite (SO₃⁻), amine, an NSAID, an aliphatic, aryl, or aryl-aliphatic substituted or unsubstituted hydrocarbon, or a biomolecule, and $M_c^{+x}$ is a pharmaceutically acceptable cation, wherein x is the valence of the cation, and c is the smallest integer that results in a neutral compound. Examples of these compounds include Angeli's salt, where J is oxide, and sulfi/NO, where J is sulfite. In some specific cases J is alkyl, such as lower, alkyl, for example methyl, ethyl, n-propyl, isopropyl, n-butyl, isobutyl, secondary-butyl, tertiary butyl (t-butyl), cyclopropyl, or cyclobutyl. In other cases J is aryl, for example phenyl.

Further examples of nitroxyl-donating diazeniumdiolates include diazeniumdiolates where J is an amine, for example a primary amine group (RNH) (a primary amine diazeniumdiolate). Examples of these compounds for use in the disclosed methods have the formula:

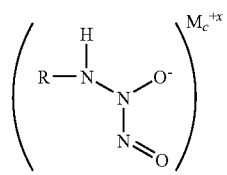

where R is an aliphatic, aryl, or aryl-aliphatic substituted or unsubstituted hydrocarbon, an NSAID, or a biomolecule, and $M_c^{+x}$ is a pharmaceutically acceptable cation, wherein x is the valence of the cation, and c is the smallest integer that results in a neutral compound. In some instances R is alkyl, for example, lower alkyl, such as methyl, ethyl, n-propyl, isopropyl, n-butyl, isobutyl, secondary-butyl, tertiary butyl (t-butyl), cyclopropyl, and cyclobutyl. In specific cases, R is isopropyl (IPA/NO) or t-butyl. In some cases R is aryl, for example phenyl. In still other cases R is aryl-aliphatic, where the aliphatic portion is alkyl, such as lower alkyl, for example ethylbenzene, n-propylbenzene, or isobutylbenzene. In specific cases, R is substituted with one or more inorganic groups, such as halogen groups, for example I, Br, Cl, or F, or nitro groups. For example, in some cases R is F substituted isopropyl, such as where R is $(CH_3CH_2F)CH_2-$), $(CH_2F)_2CH_2-$), $(CHF_2)_2CH_2-$), or $(CF_3)_2CH_2-$). In other specific cases R is an NSAID.

In general, nitroxyl-donating diazeniumdolates donate both nitroxyl and NO⁻. Nitroxyl versus NO⁻ donation by nitroxyl-donating diazeniumdiolates depends on the pH of the environment. The higher the pH the more likely the compound is to donate nitroxyl. Each nitroxyl-donating diazeniumdiolate donates nitroxyl at basic conditions (pH greater than 7, for example from a pH of greater than 7 to about 10). However, nitroxyl donation also occurs at acidic conditions (pH of less than 7) and neutral (pH of 7) conditions. For example, Angeli's salt donates nitroxyl at a pH of about 3 and greater, for example from a pH of about 3 to about 10. IPA/NO donates nitroxyl at a pH of about 5.5 and greater, for example from a pH of about 5.5 to about 10. For diazeniumdiolates, such as IPA/NO where J is a primary amine group (RNH), the nitroxyl donation pH is lower for compounds having larger R groups and/or with R groups having electron withdrawing groups such as halogen substituents. For example, the nitroxyl donation pH where R is t-butyl is lower than the nitroxyl donation pH where R is isopropyl. Also, the nitroxyl donation pH where R is isopropyl and has one or more halogen substituents, such as F, on one or more of the methyl branches, is lower than the nitroxyl donation pH where R simply is isopropyl. As human blood pH typically is about pH 7.3 to 7.4 the nitroxyl donation pH of the nitroxyl-donating diazeniumdiolates rarely will be of concern when such compounds are administered parenterally into the blood or perfused into an organ at normal physiologic pH.

However, if pH may be of concern, a nitroxyl-donating diazeniumdiolate with a donation pH below the expected pH of the site to be treated is used. Such a compound is selected based on the discussion above concerning the nitroxyl donation pHs of various compounds and/or by testing the compound for its nitroxyl donation pH as discussed below. Alternatively, the nitroxyl-donating diazeniumdiolate is administered in a buffered solution, such as with phosphate buffered saline.

In other cases the nitroxyl donor is a nitroxyl-donating S-nitrosothiol (RSNO), such as S-nitroso-L-cysteine ethyl ester, S-nitroso-L-cysteine, S-nitroso-glutathione, S-nitroso-N-acetyl-cysteine, S-nitroso-3-mercaptoethanol, S-nitroso-3-mercaptopropanoic acid, S-nitroso-2-aminonethanethiol, S-nitroso-N-acetyl penicillamine (SNAP), S-nitrosocaptopril. Wang et al., "New chemical and biological aspects of S-nitrosothiols," *Curr. Med. Chem.*, 7(8):821-34 (2000), describes nitroxyl formation from heterolytic decomposition of S-nitrosothiol compounds. In particular, S-nitrosoglutathione has been reported as capable of being reduced to nitroxyl in the presence of thiols. Hogg et al., *Biochem. J*, 323:477-481 (1997).

In other cases, the nitroxyl donor is a nitroxyl-donating hydroxamic acid (X(=O)NHOH). For example, Piloty's acid (benzenesulfohydroxamic acid; $(C_6H_5S(O)(O)NHOH)$) is used as the nitroxyl donor. In some cases other hydroxamic acids that donate nitroxyl, such as other sulfohyrdroxamic acids and their derivatives are used as nitroxyl donors. In certain specific eases, the nitroxyl donor excludes Piloty's acid.

In still other cases, the nitroxyl donor is a nitroxyl-donating thionitrate having the formula (R—(S)—NO₂), wherein R is a polypeptide, an amino acid, a sugar, a modified or unmodified oligonucleotide, a straight or branched, saturated or unsaturated, aliphatic or aromatic, substituted or unsubstituted hydrocarbon. In particular cases, such compounds that form disulfide species are used as nitroxyl donors.

In other instances the nitroxyl donor is a nitroxyl-donating oxime having the formula $(R_1R_2C=NOH)$ wherein $R_1$ and $R_2$ are, for example, hydrogen, or an aliphatic, aryl, or aryl-aliphatic substituted or unsubstituted hydrocarbon, for example where $R_1$ and $R_2$ are lower alkyl.

In some instances the nitroxyl donor is an analog and/or derivative of another nitroxyl donating compound, such as those described above. An analog is a molecule that differs in chemical structure from a parent compound, for example a homolog (differing by an increment in the chemical structure, such as a difference in the length of an alkyl chain), a molecular fragment, a structure that differs by one or more functional groups, or a change in ionization. Structural analogs are often found using quantitative structure activity relationships (QSAR), with technologies such as those disclosed in Remington: *The Science and Practice of Pharmacology*, 19th Edition (1995), chapter 28. A derivative is a biologically active molecule derived from the base structure.

Any other nitroxyl donor can be used. One source helpful for determining nitroxyl donors is METHODS IN NITRIC OXIDE RESEARCH (Feelish M. & Stamler J. eds.) John Wiley & Sons, New York (1996).

Further, compounds are easily tested for nitroxyl donation with routine experiments. Although it is impractical to directly measure whether nitroxyl is donated, several tests are accepted for determining whether a compound donates nitroxyl. For example, the compound of interest can be placed in solution, for example in water, in a sealed container. After sufficient time for disassociation has elapsed, such as from several minutes to several hours, the headspace gas is withdrawn and analyzed to determine its composition, such as by gas chromatography and/or mass spectroscopy. If the gas primarily is $N_2O$, the test is positive for nitroxyl donation and the compound is a nitroxyl donor. Nitroxyl donation also can be detected by exposing the target donor to metmyoglobin ($Mb^{3+}$). Nitroxyl reacts with $Mb^{3+}$ to form an $Mb^{2+}$—NO complex, which can be detected by changes in the ultraviolet/visible spectrum or by Electron Paramagnetic Resonance (EPR). The $Mb^{2+}$—NO complex has a EPR signal centred around a g-value of about 2. Nitric oxide, on the other hand, reacts with $Mb^{3+}$ to form an $Mb^{3+}$—NO complex that is EPR silent. Accordingly, if the candidate compound reacts with $Mb^{3+}$ to form a complex detectable by common methods such as ultraviolet/visible or EPR, then the test is positive for nitroxyl donation.

Testing for nitroxyl donation in some cases is performed at a range of pHs to determine the nitroxyl donation pH of the nitroxyl-donating compound. For example, nitroxyl donation can be tested at a range of pHs such as 1, 2, 2.5, 3, 3.5, 4, 4.5, 5, 5.5, 6, 6.5, and so on. The lowest pH at which nitroxyl donation occurs is considered the nitroxyl donation pH. After the lowest pH at which nitroxyl donation occurs in a first set of tests is found, additional tests can be performed with narrower ranges of pH around the first determined nitroxyl donation pH to obtain a more specific nitroxyl donation pH. Alternatively, a nitroxyl donation test could be performed at an initial pH at which nitroxyl donation is known to occur while performing titration with acid to determine the pH at which nitroxyl donation ceases.

Nitroxyl donors are used to prevent or reduce the injury associated with future ischemia/reperfusion. For example, administration of nitroxyl prior to the onset of ischemia can reduce tissue necrosis (the size of infarct) in at-risk tissues by about 35% or more, such as from about 35% to about 55%, for example from about 40% to about 50%. In live subjects this is accomplished by administering a therapeutically effective dose of a pharmaceutical composition comprising at least one nitroxyl donating compound to a subject prior to the onset of ischemia. In organs to be transplanted this is accomplished by administering a dose of at least one nitroxyl donating compound to the organ prior to reperfusion of the organ in the transplant recipient in a dose effective to prevent or reduce ischemia/reperfusion injury upon reperfusion of the organ in the recipient. Compositions comprising more than one nitroxyl-donating compound also could be used, for example, Angeli's salt and another diazeniumdiolate that dissociates to generate nitroxyl could be used, such as IPA/NO. The nitroxyl-donating compound also can be used in combination with other classes of therapeutic agents that are designed to minimize ischemic injury, such as beta blockers, calcium channel blockers, anti-platelet therapy or other interventions for protecting the myocardium in individuals with coronary artery disease.

The method of administering nitroxyl to live subjects includes administration of the nitroxyl-donating compound prior to the onset of ischemia. This refers only to the onset of each instance of ischemia and would not preclude performance of the method with subjects who have had prior ischemic events, i.e., the method also contemplates administration of nitroxyl-donating compounds to a subject who has had an ischemic event in the past.

Individuals can be selected who are at risk of a first or subsequent ischemic event. Examples include individuals with known hypercholesterolemia, EKG changes associated with risk of ischemia, sedentary lifestyle, angiographic evidence of partial coronary artery obstruction, echocardiographic evidence of myocardial damage, or any other evidence of a risk for a future or additional ischemic event (for example a myocardial ischemic event, such as a myocardial infarction (MI), or a neurovascular ischemia such as a cerebrovascular accident CVA). In particular examples of the method, subjects would be selected for treatment who are at risk of future ischemia, but who have no present evidence of ischemia (such as electrocardiographic changes associated with ischemia (for example, peaked or inverted T-waves or ST segment elevations or depression in an appropriate clinical context), elevated CKMB, or clinical evidence of ischemia such as crushing sub-sternal chest pain or arm pain, shortness of breath and/or diaphoresis). The nitroxyl-donating compound also could be administered prior to procedures in which myocardial ischemia may occur, for example an angioplasty or surgery (such as a coronary artery bypass graft surgery). Administration of an ischemia-reperfusion injury reducing compound could be particularly beneficial for individuals at risk for an ischemic event. Thus, a method similar to the method described above is provided in which the nitroxyl-donating compound is administered to a subject at demonstrated risk for an ischemic event. The selection of a subject with such a status could be performed by a variety of methods, some of which are noted above. For example, an individual with one of more of an abnormal EKG not associated with active ischemia, prior history of myocardial infarction, elevated serum cholesterol, etc., would be at risk for an ischemic event. Thus, an at-risk subject could be selected by physical testing or eliciting the potential subject's medical history to determine whether the subject has any indications of risk for an ischemic event. If risk is demonstrated based on the indications discussed above, or any other indications that one skilled in the art would appreciate, then the subject would be considered at demonstrated risk for an ischemic event.

Ischemia/reperfusion may damage tissues other than those of the myocardium. The method provided could be useful in reducing injury from ischemia/reperfusion in the tissue of the brain, liver, gut, kidney, bowel, or in any tissue. Selecting a person at risk for non-myocardial ischemia could include a determination of the indicators used to assess risk for myocardial ischemia. However, other factors may indicate a risk for ischemia/reperfusion in other tissues. For example, surgery patients often experience surgery related ischemia. Thus, subjects scheduled for surgery could be considered at risk for an ischemic event. The following risk factors for stroke (or a subset of these risk factors) would demonstrate a subject's risk for ischemia of brain tissue: hypertension, cigarette smoking, carotid artery stenosis, physical inactivity, diabetes mellitus, hyperlipidemia, transient ischemic attack, atrial fibrillation, coronary artery disease, congestive heart failure, past myocardial infarction, left ventricular dysfunction with mural thrombus, and mitral stenosis. Ingall, "Preventing ischemic stroke: current approaches to primary and secondary prevention," *Postgrad. Med.*, 107(6):34-50 (2000). Further, complications of untreated infectious diarrhea in the elderly can include myocardial, renal, cerebrovascular and intestinal ischemia. Slotwiner-Nie & Brandt, "Infectious diarrhea in the elderly," Gastroenterol, *Clin. N. Am.*, 30(3): 625-635 (2001). Alternatively, subjects could be selected based on risk factors for ischemic bowel, kidney or liver disease. For example, treatment would be initiated in elderly subjects at risk of hypotensive episodes (such as surgical blood loss). Thus, subjects presenting with such an indication would be considered at risk for an ischemic event. Also, other conditions that may result in ischemia such as cerebral arteriovenous malformation would be considered to demonstrate risk for an ischemic event.

The method of administering nitroxyl to organs to be transplanted includes administration of nitroxyl prior to removal of the organ from the donor, for example through the perfusion cannulas used in the organ removal process. If the organ donor is a live donor, for example a kidney donor, the nitroxyl donor can be administered to the organ donor as described above for a subject at risk for an ischemic event. In other cases the nitroxyl donor can be administered by storing the organ in a solution comprising the nitroxyl donor. For example, the nitroxyl donor can be included in the organ preservation solution, such as University of Wisconsin "UW" solution, which is a solution comprising hydroxyethyl starch substantially free of ethylene glycol, ethylene chlorohydrin and acetone (see U.S. Pat. No. 4,798,824).

In particular embodiments, the nitroxyl donating compound is nitroxyl-donating diazeniumdiolate, such as Angeli's salt. In some cases the nitroxyl-donating diazeniumdiolate is a primary amine diazeniumdiolate, such as IPA/NO. However, any nitroxyl donor having a safety profile indicating the compound would be tolerated by a subject in the amount necessary to achieve a therapeutic effect may be used, including those described above. One of ordinary skill in the art would be able to determine the safety of administering particular compounds and dosages to live subjects.

The nitroxyl donating compound can be administered in the form of a pharmaceutical composition. A pharmaceutical composition comprising an effective amount of the nitroxyl donating compound as an active ingredient could be easily prepared by standard procedures well known in the art, with pharmaceutically acceptable non-toxic solvents and/or sterile carriers, if necessary.

Nitroxyl donors could be administered, for example, orally or parenterally. In some cases, nitroxyl donors are administered directly to tissue that is desired to be protected from ischemia/reperfusion, such as by injection or by bathing the tissue in a solution including nitroxyl donors.

The dose of the nitroxyl donating compound administered to live subjects is a therapeutically effective dose. The dose of the nitroxyl donating compound administered to organs to be transplanted is a dose effective to prevent or reduce ischemia/reperfusion injury following reperfusion of the organ in the recipient. Optimizing therapy to be effective across a broad population can be performed with a careful understanding of various factors to determine the appropriate therapeutic dose, in view of the inventors' disclosure that these agents confer a protective effect if administered prior to onset of ischemia. Additional guidance is provided by the inventors' disclosure that concentrations of about 1 µM of agents donating 1 mole of nitroxyl per mole of agent were effective in the methods disclosed. Thus doses of nitroxyl donors achieving such a concentration in the tissue to be treated can be used. However, the doses contemplated for use in the disclosed methods are not limited to this concentration and can be higher or lower. For example, doses ranging from about 0.5 to about 10,000 µg/kg (body weight) or more can be used, such as from about 1 µg/kg to about 1000 µg/kg.

Example 1

The following non-limiting example demonstrates that infusion of Angeli's salt, exerts protective effects against ischemia/reperfusion injury. When compared to equimolar concentration of a pure NO donor (i.e. DEA/NO), the overall protective effect produced by Angeli's Salt infusion against reperfusion injury was more pronounced.

Methods

Animals. Male Wistar rats (n=84; body-weight 450-550 g) were housed in identical cages and were allowed access to tap water and a standard rodent diet ad libitum.

Isolated heart perfusion. Each animal was anesthetized with 1 g/kg urethane i.p. 10 min after heparin (2,500 U, i.m.) treatment. The chest was opened, and the heart was rapidly excised, placed in ice-cold buffer solution and weighed. Isolated rat hearts were attached to the perfusion apparatus and retrogradely perfused with oxygenated buffer solution at 37° C. The hearts were instrumented as previously described in Rastaldo et al., "P-450 metabolite of arachidonic acid mediates bradykinin-induced negative inotropic effect," Am. J. Physiol., 280:H2823-H2832 (2001), and Paolocci et al. "cGMP-independent inotropic effects of nitric oxide and peroxynitrite donors: potential role for nitrosylation," Am. J. Physiol., 279: H1982-H1988 (2000). The flow was maintained constant (9±2 mL/min/g wet weight) to reach a typical coronary perfusion pressure of 85-90 mm Hg. A constant proportion of 10% of the flow rate was applied by means of one of two perfusion pumps (Terumo, Tokyo, Japan) using a 50 mL syringe connected to the aortic cannula. Drug applications (see Experimental Protocols) were performed by switching from the syringe containing buffer alone to the syringe of the other pump containing the drug dissolved in the vehicle at a concentration 10× to the desired final concentration in the heart. A small hole in the left ventricular wall allowed drainage of the thebesian flow, and a polyvinyl-chloride balloon was placed into the left ventricle and connected to an electromanometer for recording of left ventricular pressure (LVP). The hearts were electrically paced at 280-300 bpm and kept in a temperature-controlled chamber (37° C.). Coronary perfusion pressure (CPP) and coronary flow were monitored with a second electromanometer and an electromagnetic flow-probe, respectively, both placed along the perfusion line. Left ventricular pressure, coronary flow and coronary perfusion pressure were recorded using a TEAC R-71 recorder, digitized at 1000 Hz and analyzed off-line with DataQ-Instruments/CODAS software, which allowed quantification of the maximum rate of increase of LVP during systole ($dP/dt_{max}$).

Hearts were perfused with Krebs-Henseleit solution gassed with 95% $O_2$ and 5% $CO_2$ of the following composition: 17.7 mM sodium bicarbonate, 127 mM NaCl, 5.1 mM KCl, 1.5 mM $CaCl_2$, 1.26 mM $MgCl_2$, 11 mM D-glucose, supplemented with 5 µg/mL lidocaine.

Experimental Compounds. The nitroxyl donor Angeli's salt (AS) (sodium trioxodinitrate, $Na_2N_2O_3$) was obtained from Dr. Jon Fukuto (University of California, Los Angeles, Calif.). The NO donor DEA/NO ($NaEt_2NN(O)NO$) was synthesized as previously described by Maragos et al., "Complexes of NO with nucleophiles as agents for the controlled biological release of nitric oxide," J. Med. Chem. 34:3242-3247 (1991). Stock solutions (100 mM in 10 mM NaOH) of these compounds were diluted in buffer immediately prior to use. All other chemicals were purchased from Sigma (Milan, Italy).

Experimental Protocols. Hearts were allowed to stabilize for 30 min, and baseline parameters were recorded. Typically, coronary flow was adjusted within the first 10 min and kept constant from thereon. After 30 min stabilization, hearts were randomly assigned to one of the treatment groups reported below (n=12 in each group), and then subjected to 30 min global, no-flow ischemia, followed by 30 min of reperfusion (I/R) (see FIG. 1). Pacing of the hearts was stopped at the beginning of the ischemic period and restarted after the third minute of reperfusion.

Hearts in the control group (Group 1) were perfused with buffer for an additional 29 min after stabilization. Group 2 hearts were exposed to AS (1 µM final concentration) for 19 min followed by a 10 min buffer wash-out period. Group 3 hearts were exposed to DEA/NO (0.5 µM final concentration) administered in the same manner as AS. The concentration of DEA/NO was only one half of that of AS since DEA/NO releases up to two moles of NO⁻ per mole of donor molecule. In Group 4, a train of three cycles of 3 min global ischemia followed by 5 min of reperfusion was applied after the stabilization phase, followed by a final 10 min buffer wash-out period (IPC protocol).

Group 5 hearts were exposed to the vehicle (NaOH, final concentration 100 nM) used to dissolve both AS and DEA/NO. To test the influence of switching the myocardial redox state on AS-induced effects, in an additional group of hearts (Group 6) AS was co-infused with N-acetyl-L-cysteine (NAC, 4 mM final concentration). For comparison, hearts were also exposed to NAC alone (Group 7). The NAC dose was identical to the one previously shown to block IPC effects in isolated rat hearts by Chen et al., "A redox-based mechanism for cardioprotection induced by ischemic preconditioning in perfused rat hearts," *Circ. Res.*, 77(2):424-9 (1995), and was able to prevent IPC effects in the present study as well (data not shown). In all hearts pacing was suspended at the onset of ischemia and restarted 3 minutes following reperfusion. As isolated heart preparations may deteriorate over time (typically after 2-2.5 hrs perfusion), in the present study the re-flow duration was limited to 30 min in order to minimize the effects produced by crystalloid perfusion on heart performance, and consistently with other reports.

Assessment of ventricular function. To obtain the maximal developed LVP, the volume of the intra-ventricular balloon was adjusted to an end-diastolic LVP of 10 mm Hg during the stabilization period, as reported in Paolocci, supra, and Hare et al., "Pertussis toxin-sensitive G proteins influence nitric oxide synthase III activity and protein levels in rat hearts," *J. Clin. Invest.*, 101: 1424-31 (1998). Changes in developed LVP, $dP/dt_{max}$ and the end-diastolic value induced by the I/R protocol were continuously monitored. The difference between the end-diastolic LVP (EDLVP) before the end of the ischemic period and during pre-ischemic conditions was used as an index of the extent of contracture development. Maximal recovery of developed LVP and $dP/dt_{max}$ during reperfusion was compared with respective pre-ischemic values.

Assessment of myocardial injury. Enzyme release is a measure of severe myocardial injury that has yet to progress to irreversible cell injury. Samples of coronary effluent (2 mL) were withdrawn with a catheter inserted into the right ventricle via the pulmonary artery. Samples were taken immediately before ischemia and at 3, 6, 10, 20 and 30 min of reperfusion. LDH release was measured as previously described by Bergmeyer & Bernt, "Methods of Enzymatic Analysis," *Verlag Chemie* (1974). Data are expressed as cumulative values for the entire reflow period.

To corroborate the data relative to myocardial injury, determined by LDH release, infarct areas were also assessed in a blinded fashion. At the end of the course (30 min reperfusion), each heart was rapidly removed from the perfusion apparatus, and the LV dissected into 2-3 mm circumferential slices. Following 15 min of incubation at 37° C. in 0.1% solution of nitro blue tetrazolium in phosphate buffer as described in Ma et al., "Opposite effects of nitric oxide and nitroxyl on postischemic myocardial injury," *Proc. Natl. Acad. Sci.*, 96:14617-14622 (1999), unstained necrotic tissue was separated from the stained viable tissue. The areas of viable and necrotic tissue were carefully separate by and independent observer (D. Mancardi, C. Penna, or R. Rastaldo) who was not aware of the origin of the hearts. The weight of the necrotic and non-necrotic tissues was then determined and the necrotic mass expressed as a percentage of total left ventricular mass.

Cardiac weight (1.35±0.03 g; n=84) and cardiac to body weight ratio (0.003±0.00005; n=84) were equivalent among the five treatment groups.

Statistical Analysis. All values are presented as means±SEM. All data were subjected to ANOVA followed by the Bonferroni correction for post hoc t tests. Significance was accepted at a p level of <0.05.

Results

Pre-ischemic function. Table 1 displays baseline cardiac function after stabilization, and prior to ischemia for the 7 animal groups. There were no significant differences among groups.

TABLE 1

| | End of stabilization period | | | | | | |
|---|---|---|---|---|---|---|---|
| | Control | AS | DEA/NO | IPC | Vehicle | NAC | NAC + AS |
| CPP (mmHg) | 85 ± 5 | 89 ± 4 | 91 ± 4 | 88 ± 9 | 92 ± 5 | 88 ± 3 | 84 ± 4 |
| LVEDP (mmHg) | 8 ± 0.6 | 9 ± 0.7 | 8 ± 0.7 | 11 ± 0.5 | 9 ± 0.7 | 8 ± 0.8 | 10 ± 0.9 |
| Developed LVP (mmHg) | 89 ± 7 | 99 ± 6 | 98 ± 5 | 85 ± 6 | 88 ± 8 | 89 ± 7 | 96 ± 7 |
| $DP/dt_{max}$ (mmHg/s) | 2794 ± 212 | 3145 ± 155 | 3047 ± 120 | 2692 ± 66 | 2661 ± 101 | 2760 ± 216 | 3011 ± 195 |

| | Post-treatment (pre-ischemic) | | | | | | |
|---|---|---|---|---|---|---|---|
| | Control | AS | DEA/NO | IPC | Vehicle | NAC | NAC + AS |
| CPP (mmHg) | 87 ± 5 | 88 ± 6 | 90 ± 4 | 93 ± 8 | 94 ± 7 | 88 ± 4 | 82 ± 4 |
| LVEDP (mmHg) | 9 ± 0.6 | 10 ± 0.8 | 9 ± 0.7 | 11 ± 1.6 | 10 ± 0.8 | 10 ± 1.7 | 10 ± 0.9 |

TABLE 1-continued

| | | | | | | | |
|---|---|---|---|---|---|---|---|
| Developed LVP (mmHg) | 88 ± 8 | 98 ± 7 | 99 ± 6 | 83 ± 6 | 88 ± 8 | 86 ± 6 | 93 ± 3 |
| $DP/dt_{max}$ (mmHg/s) | 2649 ± 151 | 3223 ± 147 | 2976 ± 93 | 2634 ± 67 | 2701 ± 103 | 2481 ± 245 | 2714 ± 187 |

CPP, coronary perfusion pressure; LVEDP, left ventricular end-diastolic pressure; LVP, left ventricular pressure; $dP/dt_{max}$, maximum rate of increase of LVP during systole; AS, Angeli's salt; DEA/NO, diethylamine diazeniumdiolate (nitric oxide donor); IPC, ischemic preconditioning; NAC, N-acetyl-L-cysteine.

Figure 2A:
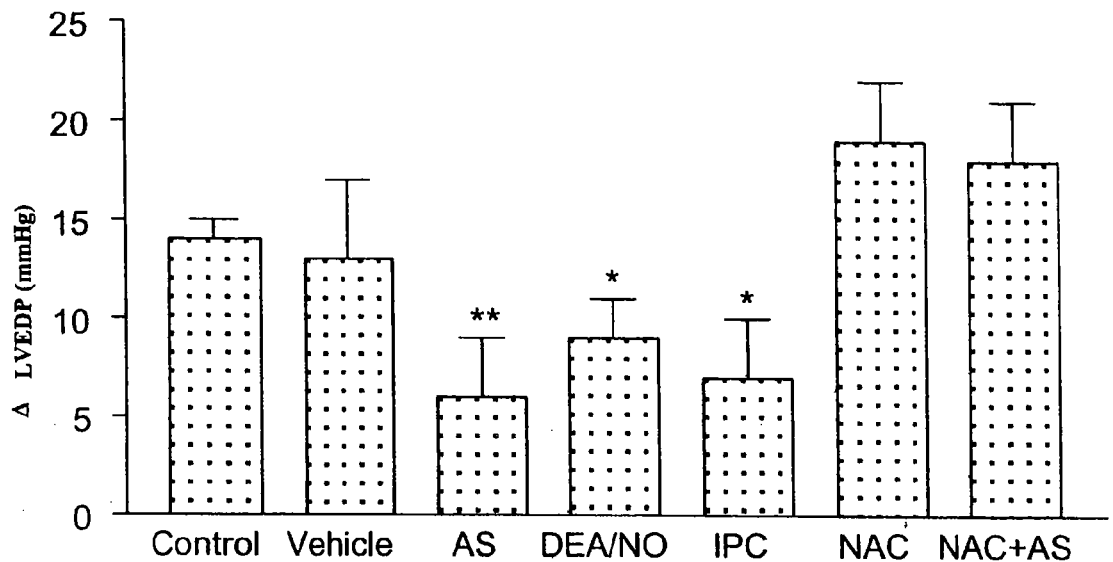

Contracture development during ischemia. The development of contracture started after 15±2 min of global ischemia in control hearts and after 15±1 min in the vehicle group. This effect was somewhat delayed (17-20 min; p=NS vs controls) in all other groups. As shown in FIG. 2A, at the end of the ischemic period LEDVP was between 24 and 28 mmHg in control hearts, vehicle-, NAC-, and NAC+AS-treated groups, with no statistically significant differences among this groups. In contrast, at the same time point AS, DEA/NO and IPC hearts showed LVEDP values ranging from 16 to 19 mmHg (p=NS between these groups) that were statistically lower that those reported in control, vehicle-, NAC- and NAC+AS-treated hearts (p<0.05 for all).

Figure 2B:
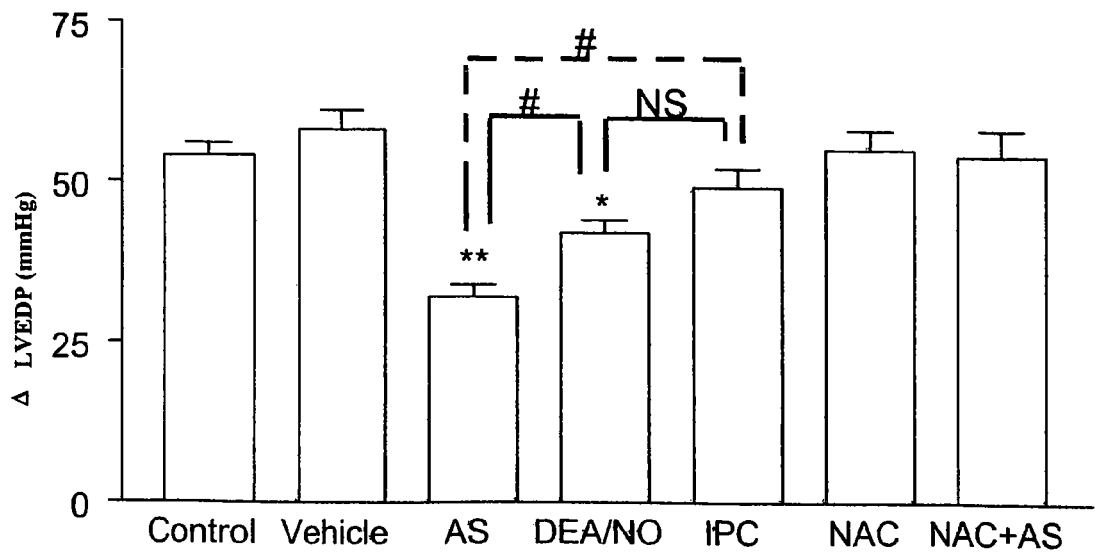
FIG. 2B is a graph showing the change in LVEDP between the peak level at reperfusion and the pre-ischemic values for interventions in the same isolated rat hearts as in FIG. 2A. Data are means±SEM. *$p<0.05$ and **$p<0.01$ vs. controls; # $p<0.05$ vs. IPC. NS=not significant.

Contracture development during reperfusion. At reperfusion LVEDP further increased. As shown in FIG. 2B, the maximal increment during reperfusion was significantly lower in AS and DEA/NO treated hearts when compared to control, vehicle, NAC and NAC+AS (p<0.05) treated hearts. AS was even more effective than DEA/NO in preventing LVEDP increase (p<0.001). In the IPC group, the development of contracture showed a trend to decrease, although not significantly, with respect to control hearts.

Figure 3A:
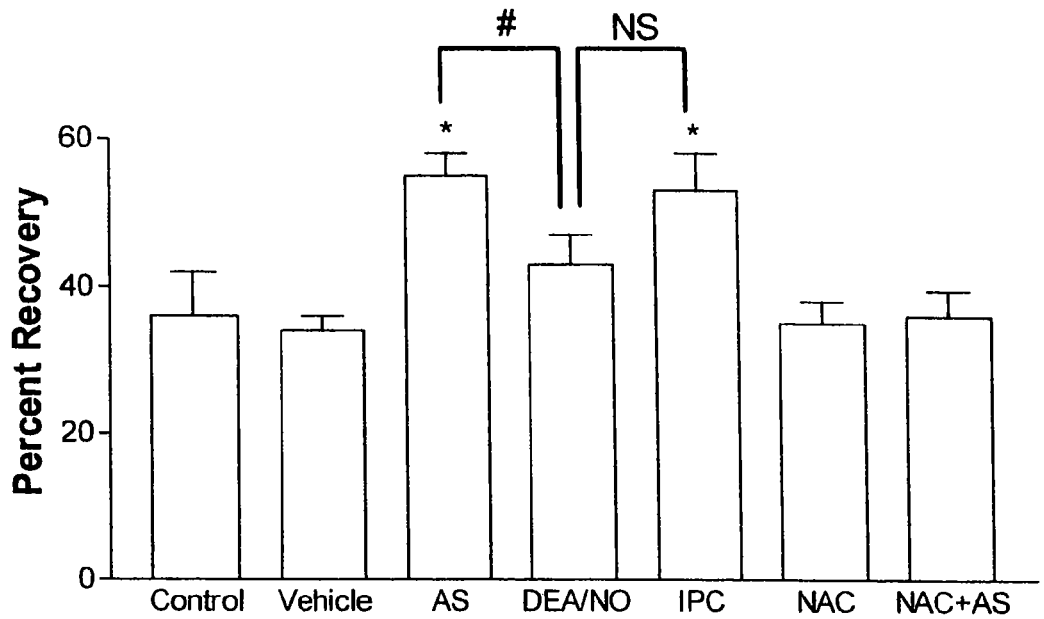
FIG. 3A is a graph showing the post-ischemic recovery: of developed left ventricular pressure (LVP) for interventions in the same isolated rat hearts as in FIG. 2.
Figure 3B:
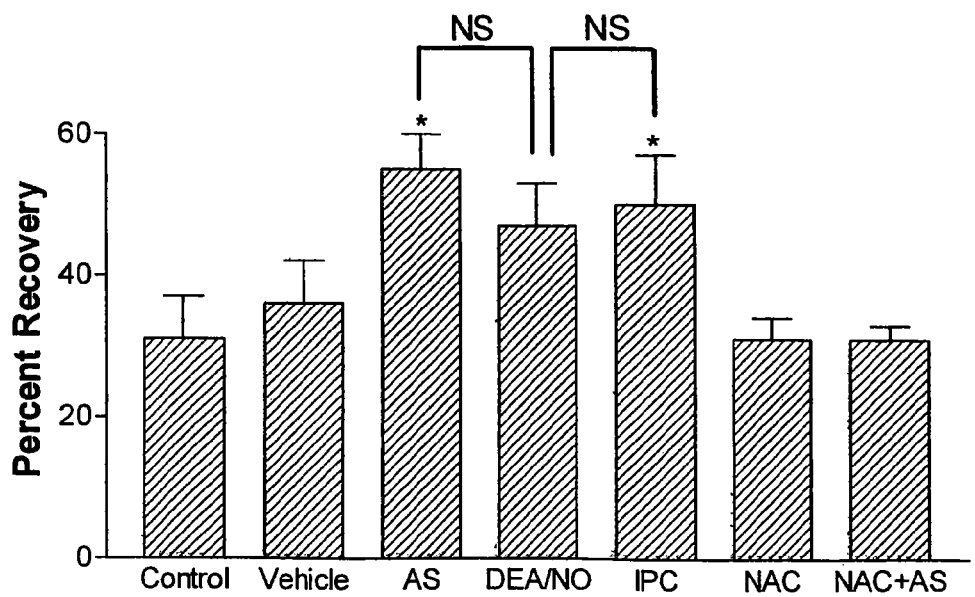
FIG. 3B is a graph showing the recovery of maximum rate of increase in LVP during systole ($dP/dt_{max}$) following 30 min global, no-flow ischemia and 30 min reperfusion for the same isolated rat hearts as in FIG. 2. Data are means±SEM. *$p<0.05$ vs. controls.

Post-ischemic contractile function. LV contractile function, indexed by developed LVP and $dP/dt_{max}$, was found to be impaired in all groups at reperfusion. However, as seen in FIGS. 3A and 3B, the recovery from myocardial stunning observed in control, NAC-, NAC+AS and vehicle-treated hearts was significantly improved by AS. Developed pressure with AS was about 55% vs 38% for controls, and +dP/dt max was 57% vs 39% in controls. Similarly, IPC increased developed. LVP when compared to controls with IPC hearts at about 53% vs. 38% for controls, as well as $dP/dt_{max}$ which was about 55% with IPC and 30% in controls (FIGS. 3A and B). In contrast, DEA/NO was less effective in recovering contractile function from that observed in control group (p=0.08 for $dP/dt_{max}$ and p=0.07 for developed LVP).

Figure 4A:
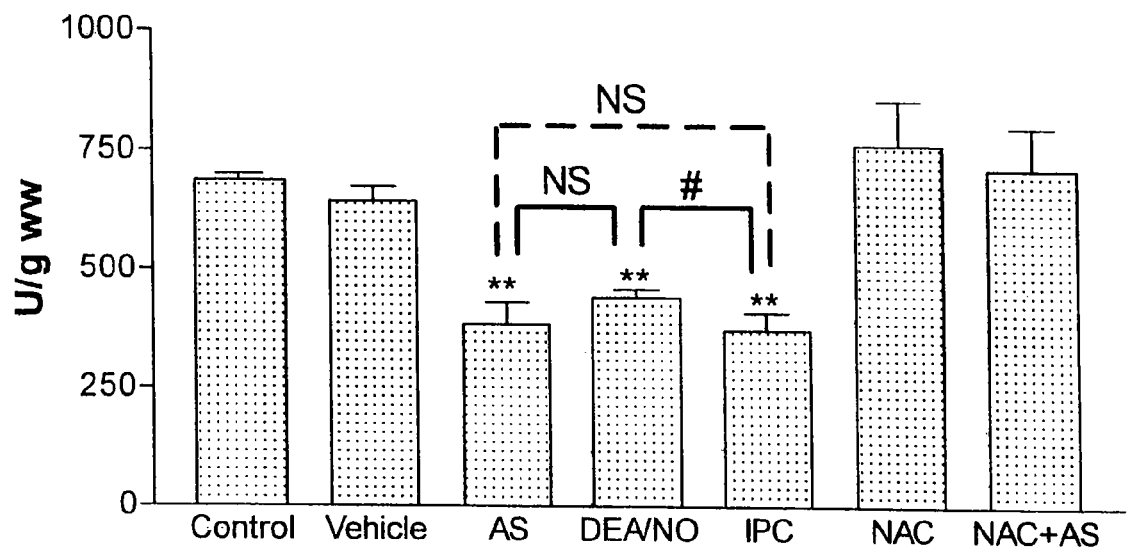
FIG. 4A is a graph showing post-ischemic leakage of lactate dehydrogenase (LDH) following 30 min of global ischemia and 30 min reperfusion for the same isolated rat hearts as FIG. 2.
Figure 4B:
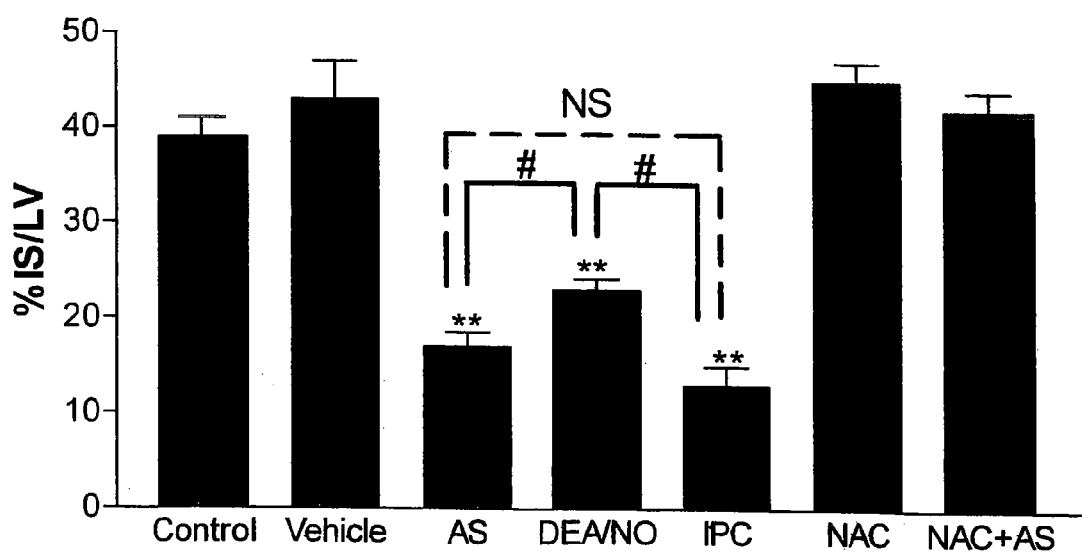
FIG. 4B shows infarct size (IS) following 30 min of global ischemia and 30 min reperfusion for the same isolated rat hearts as in FIG. 2. LV=left ventricle. Data are means±SEM. *$p<0.05$ vs. vehicle group, # $p<0.05$ vs. IPC, §$p<0.05$ vs. AS; NS=not significant.

Myocardial necrosis after reperfusion. During reperfusion, LDH release into the coronary venous effluent was 686±14 U/g wet wt from control heart group. As shown in FIG. 4A, LDH release was significantly reduced by DEA/NO, AS and IPC pre-treatment. However, AS-induced attenuation was significantly more pronounced that that provided by DEA/NO. The infracted area (FIG. 4), expressed as a percentage of the left ventricle, was 39±2%, 42±4%, 45±2% and 42±2% in the control, vehicle, NAC and NAC+AS groups, respectively (p=NS among these groups). In contrast, when compared to controls, both AS and IPC reduced infarct size significantly, by 55% and 67% respectively (p<.01 for both vs controls), with insignificant difference between them (p=0.08). Interestingly, the protective effect of DEA/NO was significantly weaker (–30%; p<0.05 vs controls) than that provided by either AS or IPC (p<0.05 vs both).

Example 2

Figure 5:
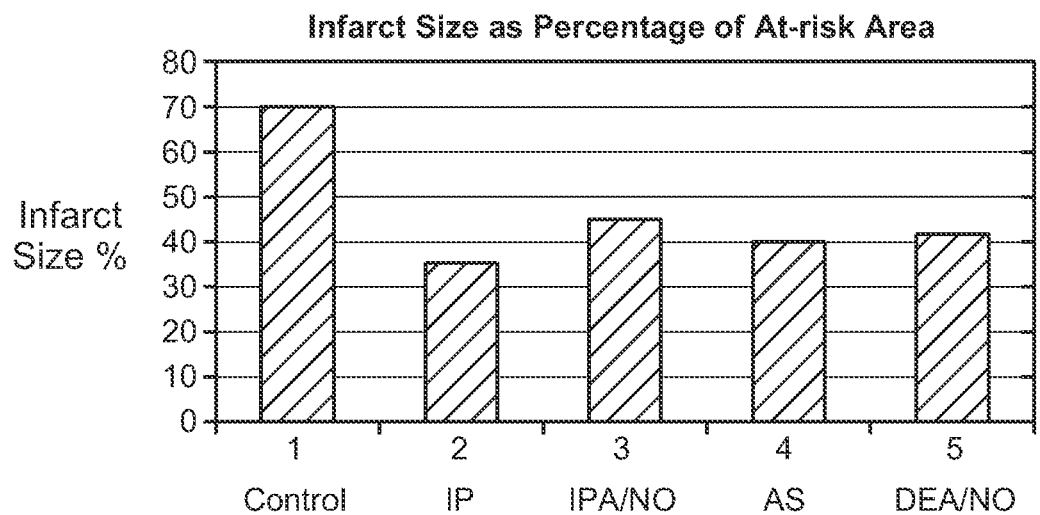
FIG. 5 is a graph showing infarct size following 30 min of global ischemia and 30 min reperfusion for interventions in a different set of isolated rat hearts for interventions with control; ischemic preconditioning (IP); IPA/NO; AS and DEA/NO.
Figure 6:
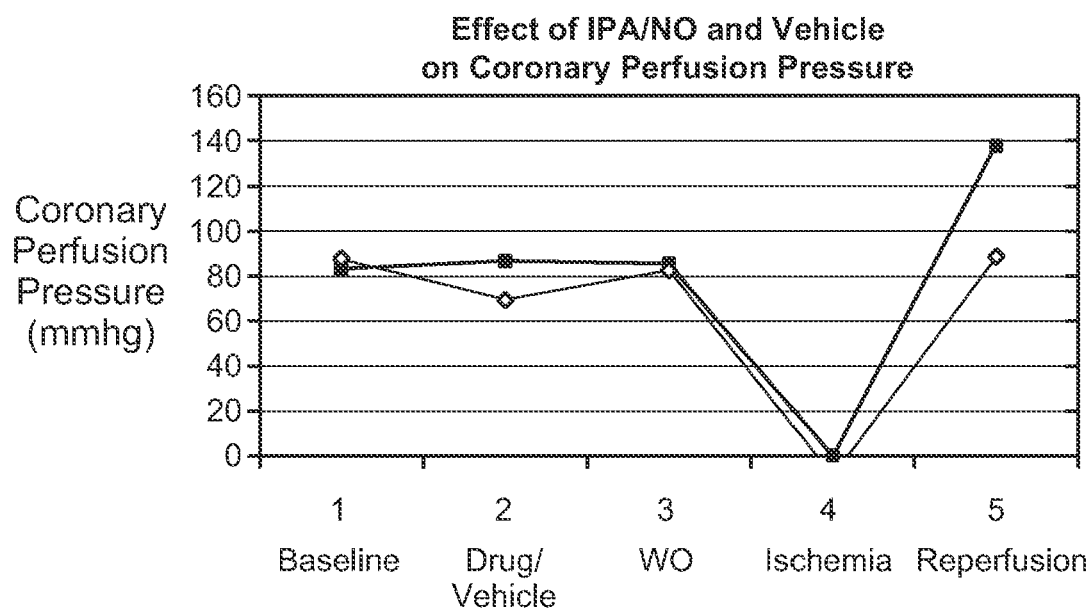
FIG. 6 is a graph showing the coronary perfusion pressures for the IPA/NO intervention of FIG. 5 and an intervention in an isolated rat heart with a vehicle for the same protocol as was used with AS and vehicle in FIG. 1. IPA/NO is represented by diamonds; vehicle is represented by squares.

The same methods as employed in Example 1 were used to assess the ischemia/reperfusion injury reducing effects of the nitroxyl donor IPA/NO. In this example, rat hearts were treated either with a control, ischemic preconditioning, IPA/NO, AS, or DEA/NO (only one rat heart was used per intervention in this example). The IPA/NO intervention protocol was the same as the AS protocol in Example 1. As can be seen in FIG. 5, IPA/NO had a comparable infarct size reducing effect to Angeli's salt (infarct size was reduced by about 36% as compared to control) confirming the utility of nitroxyl donors in preventing and/or reducing ischemia/reperfusion injury when administered prior to the onset of ischemia. This is reinforced by the fact that the coronary perfusion pressure returned to normal during reperfusion in the IPA/NO intervention as can be seen in FIG. 6.

The above-described examples merely provide exemplary embodiments of the provided method. They are not intended to be limiting in any way. Moreover, although embodiments of the method provided have been described herein in detail, it will be understood by those of skill in the art that variations may be made thereto without departing from the spirit of the invention or scope of the appended claims.

We claim:

1. A method of reducing ischemia/reperfusion injury comprising;
    selecting a subject at risk for an ischemic event; and
    administering to a subject a therapeutically effective dose of at least one nitroxyl anion donating compound wherein the compound is administered prior to the onset of ischemia.

2. The method of claim 1, wherein the nitroxyl anion donating compound is a nitroxyl-donating diazeniumdiolate.

3. The method of claim 2, wherein the nitroxyl-donating diazeniumdiolate has the formula

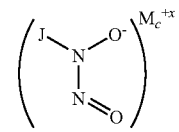

wherein J is oxide, sulfite ($SO_3^-$), amine, an NSAID, an aliphatic, aryl, or aryl-aliphatic substituted or unsubstituted hydrocarbon, or a biomolecule and $M_c^{+x}$ is a pharmaceutically acceptable cation, wherein x is the valence of the cation, and c is the smallest integer that results in a neutral compound.

4. The method of claim 3, wherein J is oxide.

5. The method of claim 3, wherein J is lower alkyl.

6. The method of claim 3, wherein J is amine.

7. The method of claim 6, wherein J is primary amine.

8. The method of claim 7, wherein the nitroxyl-donating diazeniumdiolate has the formula

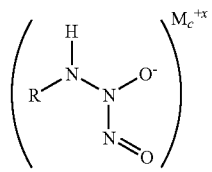

where R is an aliphatic, aryl, or aryl-aliphatic substituted or unsubstituted hydrocarbon, an NSAID, or a biomolecule and $M_c^{+x}$ is a pharmaceutically acceptable cation, wherein x is the valence of the cation, and c is the smallest integer that results in a neutral compound.

9. The method of claim 8, wherein R is alkyl.
10. The method of claim 9, wherein R is lower alkyl.
11. The method of claim 10, wherein R is isopropyl.
12. The method of claim 1, wherein the ischemia/reperfusion injury is an injury of the myocardium or brain.
13. The method of claim 12, wherein the ischemia/reperfusion injury is an injury of the myocardium.
14. The method of claim 13, wherein the size of infarction is reduced by about 35% or more.
15. The method of claim 14, wherein the size of infarction is reduced by about 35% to about 55%.
16. The method of claim 1, wherein selecting a subject at risk of an ischemic event comprises selecting a subject with no evidence of current ischemia.
17. A method of reducing ischemia/reperfusion injury comprising, administering a dose of at least one nitroxyl donating compound to an organ that is to be transplanted, wherein the dose is effective to reduce ischemia/reperfusion injury upon reperfusion of the organ in a recipient.
18. The method of claim 17, wherein the nitroxyl anion donating compound is a nitroxyl-donating diazeniumdiolate.
19. The method of claim 18, wherein the nitroxyl-donating diazeniumdiolate has the formula

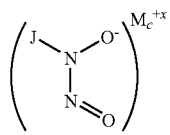

wherein J is oxide, sulfite, amine, an NSAID, an aliphatic, aryl, or aryl-aliphatic substituted or unsubstituted hydrocarbon, or a biomolecule and $M_c^{+x}$ is a pharmaceutically acceptable cation, wherein x is the valence of the cation, and c is the smallest integer that results in a neutral compound.

20. The method of claim 19, wherein J is oxide.
21. The method of claim 19, wherein J is lower alkyl.
22. The method of claim 19, wherein J is amine.
23. The method of claim 22, wherein J is primary amine.
24. The method of claim 23, wherein the nitroxyl-donating diazeniumdiolate has the formula

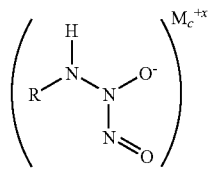

where R is an aliphatic, aryl, or aryl-aliphatic substituted or unsubstituted hydrocarbon, an NSAID, or a biomolecule and $M_c^{+x}$ is a pharmaceutically acceptable cation, wherein x is the valence of the cation, and c is the smallest integer that results in a neutral compound.

25. The method of claim 24, wherein R is alkyl.
26. The method of claim 25, wherein R is lower alkyl.
27. The method of claim 26, wherein R is isopropyl.
28. A method of reducing ischemia/reperfusion injury of the myocardium or brain comprising: administering to an individual who has had a prior ischemic event a therapeutically effective dose of a compound, which dose donates a therapeutically effective amount of nitroxyl under physiological conditions, wherein the compound is administered prior to the onset of an additional ischemic event of the myocardium or brain and wherein the compound produces a more pronounced protective effect relative to a compound that is a pure nitric oxide donor under physiological conditions.
29. The method of claim 28, wherein the compound is a diazeniumdiolate.
30. The method of claim 29, wherein the diazeniumdiolate has the formula

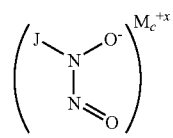

wherein J is oxide, sulfite ($SO_3^-$), amine, an NSAID, an aliphatic, aryl, or aryl-aliphatic substituted or unsubstituted hydrocarbon, or a biomolecule and $M_c^{+x}$ is a pharmaceutically acceptable cation, wherein x is the valence of the cation, and c is the smallest integer that results in a neutral compound.

31. The method of claim 30, wherein J is oxide.
32. The method of claim 30, wherein J is lower alkyl.
33. The method of claim 30, wherein J is amine.
34. The method of claim 33, wherein J is primary amine.
35. The method of claim 34, wherein the diazeniumdiolate has the formula

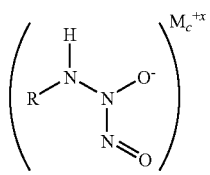

where R is an aliphatic, aryl, or aryl-aliphatic substituted or unsubstituted hydrocarbon, an NSAID, or a biomolecule and $M_c^{+x}$ is a pharmaceutically acceptable cation, wherein x is the valence of the cation, and c is the smallest integer that results in a neutral compound.

36. The method of claim 35, wherein R is alkyl.
37. The method of claim 36, wherein R is lower alkyl.
38. The method of claim 37, wherein R is isopropyl.
39. The method of claim 28, wherein the ischemia/reperfusion injury is an injury of the myocardium.
40. The method of claim 39, wherein the size of infarction is reduced by about 35% or more.

41. The method of claim 40, wherein the size of infarction is reduced by about 35% to about 55%.

42. The method of claim 28, wherein the individual does not exhibit evidence of current ischemia.

43. The method of claim 28, wherein the individual has hypercholesterolemia.

44. The method of claim 28, wherein the individual exhibits EKG changes associated with risk of ischemia.

45. The method of claim 28, wherein the individual has a sedentary lifestyle.

46. The method of claim 28, wherein the individual has partial coronary artery obstruction.

47. The method of claim 28, wherein the individual has myocardial damage.

48. The method of claim 28, wherein the individual is at risk of a future myocardial ischemic event.

49. The method of claim 48, wherein the mycocardial ischemic event is a myocardial infarction.

50. The method of claim 28, wherein the individual is at risk of a future neurovascular ischemic event.

51. The method of claim 50, wherein the neurovascular ischemic event is a cerebrovascular accident.

52. The method of claim 28, wherein the compound is administered to the individual prior to surgery.

53. The method of claim 28, wherein the compound is administered to the individual prior to an angioplasty.

54. The method of claim 28, wherein the individual exhibits one or more risk factors associated with stroke.

55. The method of claim 28, wherein the individual has a condition or habit selected from the group consisting of hypertension, cigarette smoking, carotid artery stenosis, physical inactivity, diabetes mellitus, hyperlipidemia, transient ischemic attack, atrial fibrillation, coronary artery disease, congestive heart failure, past myocardial infarction, left ventricular dysfunction with mural thrombus, and mitral stenosis.

56. The method of claim 28, wherein the individual is elderly and at risk of a hypotensive episode.

* * * * *